US012690790B2

(12) United States Patent
Jiao et al.

(10) Patent No.: US 12,690,790 B2
(45) Date of Patent: Jul. 28, 2026

(54) HAND-EYE COLLABORATIVE AUDITORY COGNITIVE ASSESSMENT SYSTEM

(71) Applicants:The Twelfth People's Hospital Affiliated to Guangzhou Medical University, Guangzhou (CN); GUANGZHOU MEDICAL UNIVERSITY, Guangzhou (CN)

(72) Inventors: Yuenong Jiao, Guangzhou (CN); Linlan Jiang, Guangzhou (CN); Liwen Wang, Guangzhou (CN); Shuyi Gao, Guangzhou (CN)

(73) Assignees: The Twelfth People's Hospital Affiliated to Guangzhou Medical University, Guangzhou (CN); GUANGZHOU MEDICAL UNIVERSITY, Guangzhou (CN)

( * ) Notice: Subject to any disclaimer, the term of this patent is extended or adjusted under 35 U.S.C. 154(b) by 0 days.

(21) Appl. No.: 18/995,240

(22) PCT Filed: Nov. 8, 2024

(86) PCT No.: PCT/CN2024/130753
§ 371 (c)(1),
(2) Date: Jan. 16, 2025

(87) PCT Pub. No.: WO2025/077929
PCT Pub. Date: Apr. 17, 2025

(65) Prior Publication Data
US 2026/0000326 A1     Jan. 1, 2026

(51) Int. Cl.
*A61B 5/16*         (2006.01)
*A61B 5/00*         (2006.01)
(Continued)

(52) U.S. Cl.
CPC ............ *A61B 5/162* (2013.01); *A61B 5/1104* (2013.01); *A61B 5/4803* (2013.01); *A61B 5/742* (2013.01); *G10L 15/22* (2013.01); *G10L 25/66* (2013.01)

(58) Field of Classification Search
CPC ..... A61B 5/162; A61B 5/1104; A61B 5/4803; G10L 25/66
See application file for complete search history.

(56) References Cited

U.S. PATENT DOCUMENTS

| | | | |
|---|---|---|---|
| 2008/0091628 | A1 | 4/2008 | Srinivasa et al. |
| 2014/0178843 | A1 | 6/2014 | Smyth |

(Continued)

FOREIGN PATENT DOCUMENTS

| | | |
|---|---|---|
| CN | 103239236 A | 8/2013 |
| CN | 104661713 A | 5/2015 |

(Continued)

OTHER PUBLICATIONS

Notice of Allowance of counterpart Chinese Patent Application No. 202311326609.3 issued on Jan. 3, 2025.

(Continued)

*Primary Examiner* — Carl H Layno
*Assistant Examiner* — Bryan McAllister Lee

(57)     ABSTRACT

A hand-eye collaborative auditory cognitive assessment system includes: a speech recognition device configured to provide speech information to a participant, obtain a retold statement, and obtain a speech retelling result; a hand-eye recognition device configured to provide visual information to the participant; obtain hand movement information of the participant, where the hand movement information includes a single hand movement score and a comprehensive hand movement score, the single hand movement score is obtained when the hand-eye recognition device operates (Continued)

alone, and the comprehensive hand movement score is obtained when the speech recognition device and the hand-eye recognition device operate together; and process the single hand movement score and the comprehensive hand movement score to obtain a cognitive scoring result; and an assessment processing device configured to perform cognitive assessment on the participant based on the speech retelling result and the cognitive scoring result. The disclosure improves cognitive assessment efficiency.

10 Claims, 3 Drawing Sheets

(51) Int. Cl.
 A61B 5/11  (2006.01)
 G10L 15/22  (2006.01)
 G10L 25/66  (2013.01)

(56) References Cited

U.S. PATENT DOCUMENTS

| | | | |
|---|---|---|---|
| 2017/0150907 A1 | 6/2017 | Duffy |
| 2019/0313967 A1 | 10/2019 | Lee |

| 2020/0029885 A1 | 1/2020 | Yanagi |
| 2021/0236044 A1 | 8/2021 | Arroyo-Gallego et al. |
| 2021/0312942 A1 | 10/2021 | Rudzicz et al. |

FOREIGN PATENT DOCUMENTS

| CN | 106999103 A | | 8/2017 | |
|---|---|---|---|---|
| CN | 108962397 A | * | 12/2018 | ............. G16H 50/20 |
| CN | 111493883 A | | 8/2020 | |
| CN | 112768071 A | | 5/2021 | |
| CN | 114983344 A | | 9/2022 | |
| CN | 116251293 A | | 6/2023 | |
| RU | 2798703 C1 | | 6/2023 | |
| WO | 2013012315 A1 | | 1/2013 | |

OTHER PUBLICATIONS

First Office Action of counterpart Chinese Patent Application No. 202311326609.3 issued on Nov. 6, 2024.

* cited by examiner

| Participant | Single task | Silent state | | | 0dB | | | 5dB | | | 10dB | | | 15dB | | |
| | Hand-eye collaborative tracking ability test (HECAT) score | Secondary task | Listening effort | Speech recognition rate | Secondary task | Listening effort | Speech recognition rate | Secondary task | Listening effort | Speech recognition rate | Secondary task | Listening effort | Speech recognition rate | Secondary task | Listening effort | Speech recognition rate |
|---|---|---|---|---|---|---|---|---|---|---|---|---|---|---|---|---|
| N1 | 98 | 86 | 12 | 67% | 65 | 33 | 45% | 72 | 26 | 58% | 80 | 18 | 65% | 82 | 16 | 67% |
| N2 | 98 | 97 | 1 | 82% | 93 | 5 | 60% | 96 | 2 | 73% | 94 | 4 | 80% | 96 | 2 | 80% |

FIG. 3

HAND-EYE COLLABORATIVE AUDITORY COGNITIVE ASSESSMENT SYSTEM

TECHNICAL FIELD

The present disclosure relates to the technical field of cognitive assessment devices, and in particular, to a hand-eye collaborative auditory cognitive assessment system.

BACKGROUND

Auditory perception is one of most important senses of living things. Human perception of sound requires not only hearing, but also understanding, that is, understanding of speech. In order to recognize a speech signal in an environment, a listener first needs to extract a target speech signal from interfering background noise through auditory scene analysis and selective attention. In the auditory scene analysis, different auditory sources in an auditory scene are recognized based on binaural clues, spectral clues, and time clues. Then, attention is focused on a selected speech signal, while other signals are ignored. Once the attention is focused on the target signal, the listener compares the extracted speech signal with a representation in a semantic long-term memory. If the extracted signal matches the representation in the semantic long-term memory, a vocabulary can be quickly and correctly extracted, and an incoming speech signal is also easily recognized and understood. But actually, a hearing loss or a cognitive decline exists. When the hearing loss occurs, the incoming speech signal may attenuate and cannot be quickly recognized. A listener with the cognitive decline is unable to match the selected speech signal with the representation in the long-term semantic memory in a timely and accurate manner, which affects judgment of the listener for the speech signal.

At present, professional physical examination devices are usually used to examine the listener with the hearing loss or the cognitive decline. It is necessary to obtain parameters of the listener, such as a brain activity, an autonomic nervous system activity, a pupillary response, a heart rate variability, a skin conductance response, and a hormone level, for synthetic judgment to determine a cause for the cognitive decline of the subject. However, related devices are expensive, which increases complexity of a detection process when a plurality of devices are used. As a result, the subject is prone to resist the complex detection process, which affects accuracy of some detection parameters and thus affects a result of cognitive assessment. The above problems need to be solved.

SUMMARY

In order to reduce an impact of a complex process on detection accuracy and improve efficiency of cognitive assessment, the present disclosure provides a hand-eye collaborative auditory cognitive assessment system. The following technical solutions are adopted:

The present disclosure provides a hand-eye collaborative auditory cognitive assessment system, including:

a speech recognition device configured to provide speech information to a participant, obtain a retold statement made by the participant based on the speech information, and obtain a speech retelling result;

a hand-eye recognition device configured to provide visual information to the participant; obtain information of a hand movement executed by the participant based on the visual information, where the information of the hand movement includes a single hand movement score and a comprehensive hand movement score, the single hand movement score is obtained when the hand-eye recognition device operates alone, and the comprehensive hand movement score is obtained when the speech recognition device and the hand-eye recognition device operate together; and process the single hand movement score and the comprehensive hand movement score to obtain a cognitive scoring result; and an assessment processing device configured to perform cognitive assessment on the participant based on the speech retelling result and the cognitive scoring result.

Preferably, the hand-eye recognition device includes:

an image display module configured to display a moving region that the participant needs to follow with a hand;

a hand information obtaining module configured to obtain precise touch time of the moving region when the image display module is touched;

a timekeeping module configured to record total touch time of the image display module;

a calculation module configured to calculate the single hand movement score or the comprehensive hand movement score based on the precise touch time and the total touch time; and a hand-eye control processing module configured to control startup and stop of the image display module, the hand information obtaining module, and the timekeeping module, and process the single hand movement score and the comprehensive hand movement score to obtain the cognitive scoring result.

Preferably, when the hand-eye recognition device provides the visual information to the participant separately, the hand-eye control processing module calculates the single hand movement score based on the precise touch time and the total touch time.

Preferably, when the hand-eye recognition device provides the visual information to the participant and the speech recognition device provides the speech information to the participant, the hand-eye control processing module calculates the comprehensive hand movement score based on the precise touch time and the total touch time.

Preferably, the speech recognition device includes:

a word and sentence database module configured to store a speech task that the participant needs to retell;

an audio output module configured to output a speech task that is to be retold by the participant; and a speech control processing module configured to control startup and stop of the word and sentence database module and the audio output module, obtain the retold statement, and compare the retold statement with the speech task output by the audio output module to obtain the speech retelling result.

Preferably, the speech recognition device further includes:

a speech rate adjustment module configured to adjust an output speech rate of the speech task of the audio output module.

Preferably, the word and sentence database module is configured to divide the speech task into a plurality of speech task groups based on an age bracket; and the audio output module is configured to obtain age information of the participant, compare the age information with a plurality of age brackets in the word and sentence database module to obtain a speech task group of an appropriate age bracket, and output the speech task based on the speech task group.

Preferably, the word and sentence database module is configured to set a corresponding output speech rate of the speech task for each speech task group; and the speech rate adjustment module is configured to obtain the age information of the participant, compare the age information with the age brackets in the word and sentence database module to obtain an output speech rate of a speech task of an appropriate age bracket, and adjust the output speech rate of the speech task of the audio output module.

Preferably, the image display module is configured to display a moving region that moves along an elliptical path.

Preferably, the hand-eye recognition device further includes:

a touch adjustment module configured to set whether the moving region of the image display module moves at a uniform speed; and when the moving region moves at the uniform speed, adjust a movement speed of the moving region along the elliptical path; or when the moving region moves at a variable speed, adjust a plurality of movement speeds of the moving region along the elliptical path, and adjust duration of a corresponding speed of the moving region.

Preferably, the speech recognition device further includes:

a noise output module configured to output preset noise and provide a plurality of signal-to-noise ratio (SNR) environments to the participant.

Preferably, when the noise output module outputs the noise, in the SNR environments, all speech tasks output by the audio output module are consistent, and all movement speeds of the moving region of the image display module are consistent.

Preferably, the hand-eye control processing module is configured to: when the single hand movement score and the comprehensive hand movement score are obtained, subtract the single hand movement score from a plurality of obtained comprehensive hand movement scores separately to obtain a plurality of listening effort scores, and then obtain the cognitive scoring result through analysis based on a change between the listening effort scores.

Preferably, the speech task stored in the word and sentence database module includes a plurality of types of long sentences, short sentences, and words; and the speech task output by the audio output module is some long sentences, short sentences, or words obtained from the word and sentence database module.

Preferably, the image display module is configured to adjust touch area of the moving region.

In conclusion, compared with the prior art, the technical solutions provided in the present application have at least following beneficial effects:

The present disclosure simultaneously provides speech information and visual information to a participant through a speech recognition device and a hand-eye recognition device, enabling the participant to process two tasks simultaneously. After obtaining the speech information, the participant orally retells a statement, and the speech recognition device obtains a speech retelling result based on a retold statement. At the same time, the participant inputs hand movement information into the hand-eye recognition device with a hand when obtaining the visual information, thereby obtaining a cognitive scoring result. Based on the speech retelling result and the cognitive scoring result, an assessment processing device comprehensively assesses a status of simultaneously completing the two tasks by the participant. Cognition of the participant is assessed based on a low operating cost and a low labor cost, such that the participant can complete the assessment in a relaxed and enjoyable manner, thereby reducing an impact of a complex process on detection accuracy and improving efficiency of cognitive assessment.

BRIEF DESCRIPTION OF THE DRAWINGS

FIG. 3 is a parameter table obtained through hand-eye recognition and speech recognition according to an embodiment of the present disclosure.

REFERENCE NUMERALS

1: speech recognition device; 2: hand-eye recognition device; 3: assessment processing device.

DETAILED DESCRIPTION

The present disclosure is further described in detail below with reference to FIG. 1 to FIG. 3. Terms used in the embodiments of the present disclosure are merely used to describe the specific embodiments, and are not intended to limit the present disclosure.

Currently, parameters of a participant, such as a brain activity, an autonomic nervous system activity, a pupillary response, a heart rate variability, a skin conductance response, and a hormone level, are usually detected by a professional instrument. However, this type of instrument is expensive and needs to assess the participant based on a plurality of parameters and a plurality of detection results, resulting in low assessment efficiency. Moreover, due to a complex detection process and long detection time, it is easy to bring bad participation experience to the participant, causing the participant to resist the complex detection process. This in turn affects accuracy of detecting some hormones and electrical signals, resulting in repeated detection and affecting assessment efficiency.

An information processing capability of a human is limited. When two or more tasks are completed simultaneously, a vast majority of brain resources are allocated to a primary task that needs to be completed, while a remaining small portion of brain resources is used to complete a secondary task that needs to be completed. When a difficulty of the primary task increases, residual resources used to complete the secondary task decrease. This results in a decline in performance of the secondary task, which represents an increase in efforts. Based on the above principle, a system in the present disclosure sets up two small game devices to seize the brain resources of the participant, assesses cognition of the participant based on scores of the two devices, thereby simplifying a complex process of a current assessment method and reducing detection steps and content. In this way, an appropriate difficulty of an assessment process can be customized based on a specific situation of the participant, which can enhance participation experience of the participant, and more accurately and efficiently assess a cognitive function of the participant at a low cost.

Figure 1:
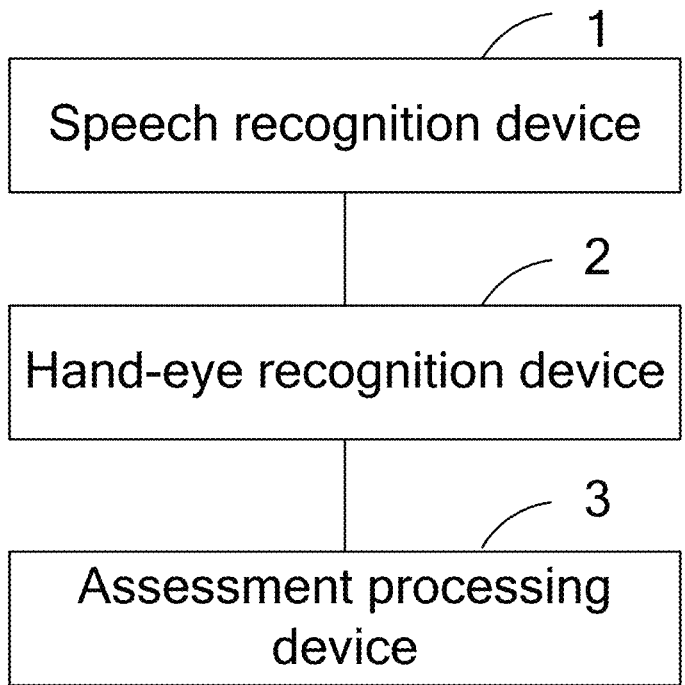
FIG. 1 is a schematic structural diagram of a hand-eye collaborative auditory cognitive assessment system according to an embodiment of the present disclosure.

With reference to FIG. 1, a hand-eye collaborative auditory cognitive assessment system involved in the present disclosure specifically includes:

a speech recognition device configured to provide speech information to a participant, obtain a retold statement, and obtain a speech retelling result;

a hand-eye recognition device configured to provide visual information to the participant; obtain information of a hand movement, where the information of the hand movement includes a single hand movement score and a comprehensive hand movement score; the single hand movement score is obtained when the hand-eye recognition device operates separately, and the comprehensive hand movement score is obtained when the speech recognition device and the hand-eye recognition device operate together; and process the single hand movement score and the comprehensive hand movement score to obtain a cognitive scoring result; and an assessment processing device configured to perform cognitive assessment on the participant based on the speech retelling result and the cognitive scoring result.

Specifically, the speech recognition device provides the speech information to the participant. The speech information is usually a pre-stored statement, word, and phrase in the speech recognition device, and is used to stimulate a hearing system of the participant through audio playback. The participant performs retelling after receiving the speech information, and the speech recognition device compares accuracy of the retold statement and the originally output speech information to obtain the speech retelling result. In addition, the hand-eye recognition device provides the visual information to the participant. The visual information is set as a moving image that can be observed by the participant. A hand of the participant swipes based on the visual information. After obtaining the information of the hand movement of the participant, the hand-eye recognition device obtains the single hand movement score and the comprehensive hand movement score. When the hand-eye recognition device operates alone, it obtains the single hand movement score. When the speech recognition device and the hand-eye recognition device operate together, the hand-eye recognition device obtains the comprehensive hand movement score, and performs processing based on the single hand movement score and the comprehensive hand movement score to obtain the cognitive scoring result. Based on the speech retelling result and the cognitive scoring result, the assessment processing device comprehensively assesses a status of simultaneously completing two tasks by the participant. Cognition of the participant is assessed based on a low operating cost and a low labor cost, such that the participant can complete the assessment in a relaxed and enjoyable manner, thereby reducing an impact of a complex process on detection accuracy and improving efficiency of the cognitive assessment.

Figure 2:
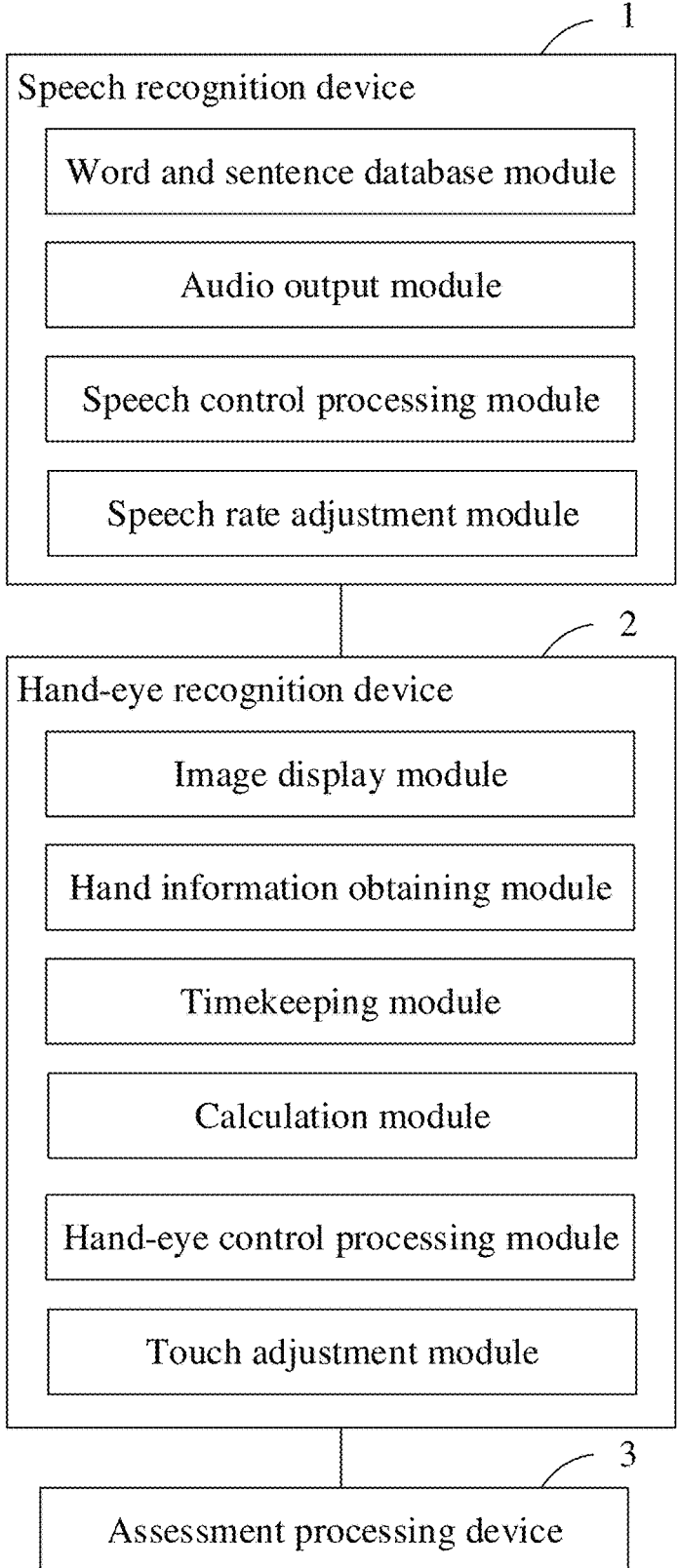
FIG. 2 is a schematic diagram of an internal structure of a hand-eye collaborative auditory cognitive assessment system according to an embodiment of the present disclosure.

Referring to FIG. 2, as an implementation, the hand-eye recognition device includes an image display module, a hand information obtaining module, a timekeeping module, a calculation module, and a hand-eye control processing module. The image display module is configured to display a moving region that the participant needs to follow with the hand. The hand information obtaining module is configured to obtain precise touch time of the moving region when the image display module is touched. The timekeeping module is configured to record total touch time of the image display module. The calculation module is configured to calculate the single hand movement score or the comprehensive hand movement score based on the precise touch time and the total touch time. The hand-eye control processing module is configured to control startup and stop of the image display module, the hand information obtaining module, and the timekeeping module, and process the single hand movement score and the comprehensive hand movement score to obtain the cognitive scoring result.

Specifically, the image display module is equipped with the moving region for the participant to touch and press. During the cognitive assessment of the hand-eye collaborative auditory cognitive assessment system, the participant obtains an image of the moving region and follows the moving region to swipe by touching the hand information obtaining module with a finger. That is, the finger of the participant touching the hand information obtaining module moves with the moving region, and the hand information obtaining module records time when the moving region is accurately touched by the participant. In addition, the timekeeping module records the total time during which the hand information obtaining module is touched, and the calculation module calculates the precise touch time and the total touch time, specifically the precise touch time/total touch time.

As an implementation, the image display module is configured to display a moving region that moves along an elliptical path.

Specifically, the moving region is a circular touch region that moves around the preset elliptical path. The circular touch region serves as a target object and continuously moves clockwise and elliptically at a constant speed. Speed and direction changes can cause interference due to individual differences in reactive potency. In the embodiments of the present disclosure, an upper speed limit of the target object is 20 revolutions per minute, a lower speed limit is 4 revolutions per minute, and a step size is 2, which means that there are 9 speed levels with a speed of 10 revolutions per minute.

As an implementation, when the hand-eye recognition device provides the visual information to the participant alone, the hand-eye control processing module calculates the single hand movement score based on the precise touch time and the total touch time.

Specifically, before the speech recognition device and the hand-eye recognition device are used simultaneously, the hand-eye recognition device needs to perform single-task detection once on the participant alone. A precise touch ratio obtained by dividing single-task precise touch time by single-task total touch time is the single hand movement score.

As an implementation, when the hand-eye recognition device provides the visual information to the participant and the speech recognition device provides the speech information to the participant, the hand-eye control processing module calculates the comprehensive hand movement score based on the precise touch time and the total touch time.

Specifically, when the speech recognition device and hand-eye recognition device are used simultaneously, the participant is interfered by the speech recognition device, and the hand-eye recognition device obtains a precise touch ratio by dividing dual-task precise touch time by dual-task total touch time, namely, the comprehensive hand movement score.

As an implementation, the speech recognition device includes a word and sentence database module, an audio output module, and a speech control processing module. The word and sentence database module is configured to store a speech task that the participant needs to retell. The audio output module is configured to output a speech task that is to be retold by the participant. The speech control processing module is configured to control startup and stop of the word and sentence database module and the audio output module, obtain the retold statement, and compare the retold statement with the speech task output by the audio output module to obtain the speech retelling result.

Specifically, the word and sentence database module stores a plurality of speech tasks. In the case of simultaneous execution of dual tasks, the speech control processing module controls the startup of the word and sentence database module and the audio output module. The audio output module can obtain the pre-stored speech task from the word and sentence database module, and the speech task specifically includes a plurality of types of long sentences, short sentences, words, and the like. The audio output module plays the speech task to the participant according to a preset rule. After receiving the speech information, the participant needs to perform the retelling within a certain period of time. The speech control processing module compares the retold statement with the speech task output by the audio output module to obtain accuracy of the speech retelling, namely, the speech retelling result. The speech information provided by the speech recognition device at this time is main information obtained by the participant.

As an implementation, the speech recognition device further includes a noise output module. The noise output module is configured to output preset noise and provide a plurality of SNR environments to the participant.

Specifically, an SNR is a difference between speech noise levels, which is a difference between intensity of a sound signal output by an audio source and intensity of simultaneously output noise and is expressed in decibels (dB). The SNR is an effective value of sound pressure of a speech signal minus an effective value of sound pressure of a noise signal. For a speech recognition task, four noisy environments with SNRs respectively being 0 dB, 5 dB, 10 dB, and 15 dB, and one quiet environment are designed. Because most of daily living environments are noisy, it is necessary to perform testing under different conditions by using a normal speech rate of 300 words per minute and controlling a speech volume to 65 dB, which is close to a speech volume of daily communication. When the noise output module outputs the noise, in the SNR environments, all speech tasks output by the audio output module are consistent, and all movement speeds of the moving region of the image display module are consistent.

As an implementation, the hand-eye control processing module is configured to: when the single hand movement score and the comprehensive hand movement score are obtained, subtract the single hand movement score from a plurality of obtained comprehensive hand movement scores separately to obtain a plurality of listening effort scores, and then obtain the cognitive scoring result through analysis based on a change between the listening effort scores.

Specifically, referring to FIG. 3, the assessment processing device performs the cognitive assessment on the participant after obtaining the speech retelling result and the cognitive scoring result. The speech retelling result shows a fluctuation of a speech recognition rate in the SNR environments. The cognitive scoring result shows a fluctuation of a listening effort in the SNR environments. The assessment processing device pre-stores a discriminant range of the speech recognition rate to determine a level of the speech recognition rate of the participant, preliminarily assesses the speech recognition rate of the participant, and then determines a listening condition of the participant based on an increase or a decrease in the speech recognition rate in each environment. The assessment processing device pre-stores a discriminant range of the listening effort to determine a level of the listening effort of the participant, preliminarily assesses the listening effort of the participant, and then determines a cognitive condition of the participant based on an increase or a decrease in the listening effort in each environment.

From FIG. 3, it can be observed that in addition to a hearing loss, a listening effort required by a participant N1 increases significantly, which indicates that a cognitive capability of the participant decreases and is greatly affected by the hearing loss. Hearing improvement and speech training may help the participant reverse a cognitive function. Although a participant N2 experiences a hearing loss, the participant N2 has a small listening effort score. Therefore, a cognitive function of the participant N2 is not greatly affected by the hearing loss. Usually, timely hearing improvement is sufficient.

As an implementation, the speech recognition device further includes a speech rate adjustment module configured to adjust an output speech rate of the speech task of the audio output module. The word and sentence database module is configured to divide the speech task into a plurality of speech task groups based on an age bracket.

The audio output module is configured to obtain age information of the participant, compare the age information with a plurality of age brackets in the word and sentence database module to obtain a speech task group of an appropriate age bracket, and output the speech task based on the speech task group.

The word and sentence database module is configured to set a corresponding output speech rate of the speech task for each speech task group. The speech rate adjustment module is configured to obtain the age information of the participant, compare the age information with the age brackets in the word and sentence database module to obtain an output speech rate of a speech task of an appropriate age bracket, and adjust the output speech rate of the speech task of the audio output module.

Specifically, the speech recognition device can improve assessment efficiency by adjusting a speech playback speed before performing a speech retelling operation. The speech rate adjustment module adjusts the audio output module to a default output speed, and gradually increases or decreases the playback speed based on an adaptation level of the participant during execution of a single speech debugging task, such that the participant can perform assessment at an appropriate speech task playback speed. An age of the participant is obtained. An appropriate speech task group is selected based on the age of the participant, and an initial value used by the speech rate adjustment module for debugging is adjusted to a value more appropriate for a current adaptation level of the participant, reducing time required for step-by-step adjustment.

As an implementation, the word and sentence database module is configured to set the corresponding output speech rate of the speech task for each speech task group. The speech rate adjustment module is configured to obtain the age information of the participant, compare the age information with the age brackets in the word and sentence database module to obtain an output speech rate of a speech task of an appropriate age bracket, and adjust the output speech rate of the speech task of the audio output module.

The hand-eye collaborative auditory cognitive assessment system further includes a touch adjustment module configured to: set whether the moving region of the image display module moves at a uniform speed; and when the moving region moves at the uniform speed, adjust a movement speed of the moving region along the elliptical path; or when the moving region moves at a variable speed, adjust a plurality of movement speeds of the moving region along the elliptical path, and adjust duration of a corresponding speed of the moving region.

Specifically, before performing a hand-eye task to obtain the visual information, the hand-eye recognition device can obtain an appropriate movement speed of the moving region based on the age when performing the hand-eye task alone. Then the touch adjustment module gradually adjusts the movement speed to a speed value and a uniform speed that are appropriate for the current participant, improving the efficiency of the cognitive assessment.

As an implementation, the image display module is configured to adjust touch area of the moving region.

Specifically, a size of the touch area of the moving region is adjusted based on the adaptation level of the participant. In this way, the participant can perform the assessment in a way that is more appropriate for the solutions in the embodiments of the present disclosure, such that the participant can complete the assessment in the relaxed and enjoyable manner. This reduces the impact of the complex process on the detection accuracy, and improves the efficiency of the cognitive assessment.

In the embodiments of the present disclosure, the speech recognition device 1, the hand-eye recognition device 2, and the assessment processing device 3 each may be one or more processors, controllers or chips that each have a communication interface, can realize a communication protocol, and may further include a memory, a related interface and system transmission bus, and the like if necessary. The processor, the controller, or the chip executes program-related code to realize a corresponding function. In an alternative solution, the speech recognition device 1, the hand-eye recognition device 2, and the assessment processing device 3 share an integrated chip or share devices such as a processor, a controller, and a memory. The shared processor, controller, or chip executes program-related code to implement a corresponding function.

In the embodiments of the present disclosure, the image display module, the hand information obtaining module, the timekeeping module, the calculation module, the hand-eye control processing module, and the touch adjustment module each may be one or more processors, controllers, or chips that each have a communication interface, can realize a communication protocol, and may further include a memory, a related interface and system transmission bus, and the like if necessary. The processor, controller, or chip executes program-related code to realize a corresponding function. In an alternative solution, the image display module, the hand information obtaining module, the timekeeping module, the calculation module, the hand-eye control processing module, and the touch adjustment module share an integrated chip or share devices such as a processor, a controller, and a memory. The shared processor, controller, or chip executes program-related code to implement a corresponding function.

In the embodiments of the present disclosure, the word and sentence database module, the audio output module, the speech control processing module, and the speech rate adjustment module each may be one or more processors, controllers, or chips that each have a communication interface, can realize a communication protocol, and may further include a memory, a related interface and system transmission bus, and the like if necessary. The processor, controller, or chip executes program-related code to realize a corresponding function. In an alternative solution, the word and sentence database module, the audio output module, the speech control processing module, and the speech rate adjustment module share an integrated chip or share devices such as a processor, a controller, and a memory. The shared processor, controller, or chip executes program-related code to implement a corresponding function.

A person skilled in the art can clearly understand that, for convenience and brevity of description, reference may be made to corresponding processes in the foregoing method embodiments for specific working processes of the foregoing devices and products. Details are not described herein again.

In several embodiments provided in the present disclosure, it should be understood that the disclosed method, system, device, and program product may be implemented in other manners.

In addition, functional units in the embodiments of the present disclosure may be integrated into one processing unit, or each of the units may exist alone physically, or two or more units are integrated into one unit. The above integrated unit may be implemented either in a form of hardware or in a form of a software functional unit.

The above embodiments are provided merely to describe the technical solutions of the present disclosure, and are not intended to limit the present disclosure. Although the present disclosure is described in detail with reference to the above embodiments, those of ordinary skill in the art should understand that they can still modify the technical solutions described in the above embodiments, or make equivalent substitutions to some technical features therein. These modifications or substitutions do not make the essence of the corresponding technical solutions depart from the spirit and scope of the technical solutions of the embodiments of the present disclosure.

The invention claimed is:

1. A hand-eye collaborative auditory cognitive assessment system, comprising:

a speech recognition device configured to provide speech information to a participant, obtain a retold statement made by the participant based on the speech information, and obtain a speech retelling result;

a hand-eye recognition device configured to provide visual information to the participant; obtain information of a hand movement executed by the participant based on the visual information, wherein the information of the hand movement comprises a single hand movement score and a comprehensive hand movement score, the single hand movement score is obtained when the hand-eye recognition device operates alone, and the comprehensive hand movement score is obtained when the speech recognition device and the hand-eye recognition device operate together; and process the single hand movement score and the comprehensive hand movement score to obtain a cognitive scoring result;

the hand-eye recognition device comprises:

an image display module configured to display a moving region that the participant requires to follow with a hand;

a hand information obtaining module configured to obtain precise touch time of the moving region when the image display module is touched;

a timekeeping module configured to record total touch time of the image display module;

a calculation module configured to calculate the single hand movement score or the comprehensive hand movement score based on the precise touch time and the total touch time; and a hand-eye control processing module configured to control startup and stop of the image display module, the hand information obtaining module, and the timekeeping module, and process the single hand movement score and the comprehensive hand movement score to obtain the cognitive scoring result;

the image display module is configured to display a moving region that moves along an elliptical path;

when the hand-eye recognition device provides the visual information to the participant separately, the hand-eye control processing module calculates the single hand movement score based on the precise touch time and the total touch time;

when the hand-eye recognition device provides the visual information to the participant and the speech recognition device provides the speech information to the participant, the hand-eye control processing module calculates the comprehensive hand movement score based on the precise touch time and the total touch time;

the hand-eye recognition device further comprises:

a touch adjustment module configured to set whether the moving region of the image display module moves at a uniform speed; and when the moving region moves at the uniform speed, adjust a movement speed of the moving region along the elliptical path; or when the moving region moves at a variable speed, adjust a plurality of movement speeds of the moving region along the elliptical path, and adjust duration of a corresponding speed of the moving region; and an assessment processing device configured to perform cognitive assessment on the participant based on the speech retelling result and the cognitive scoring result.

2. The hand-eye collaborative auditory cognitive assessment system according to claim 1, wherein the speech recognition device comprises:

a word and sentence database module configured to store a speech task that the participant requires to retell;

an audio output module configured to output a speech task that is to be retold by the participant; and a speech control processing module configured to control startup and stop of the word and sentence database module and the audio output module, obtain the retold statement, and compare the retold statement with the speech task output by the audio output module to obtain the speech retelling result.

3. The hand-eye collaborative auditory cognitive assessment system according to claim 2, wherein the speech recognition device further comprises:

a speech rate adjustment module configured to adjust an output speech rate of the speech task of the audio output module.

4. The hand-eye collaborative auditory cognitive assessment system according to claim 3, wherein the word and sentence database module is configured to divide the speech task into a plurality of speech task groups based on an age bracket; and the audio output module is configured to obtain age information of the participant, compare the age information with a plurality of age brackets in the word and sentence database module to obtain a speech task group of an appropriate age bracket, and output the speech task based on the speech task group.

5. The hand-eye collaborative auditory cognitive assessment system according to claim 4, wherein the word and sentence database module is configured to set a corresponding output speech rate of the speech task for each speech task group; and the speech rate adjustment module is configured to obtain the age information of the participant, compare the age information with the age brackets in the word and sentence database module to obtain an output speech rate of a speech task of an appropriate age bracket, and adjust the output speech rate of the speech task of the audio output module.

6. The hand-eye collaborative auditory cognitive assessment system according to claim 2, wherein the speech recognition device further comprises:

a noise output module configured to output preset noise and provide a plurality of signal-to-noise ratio (SNR) environments to the participant.

7. The hand-eye collaborative auditory cognitive assessment system according to claim 6, wherein when the noise output module outputs the noise, in the plurality of SNR environments, all speech tasks output by the audio output module are consistent, and all movement speeds of the moving region of the image display module are consistent.

8. The hand-eye collaborative auditory cognitive assessment system according to claim 7, wherein the hand-eye control processing module is configured to:

when the single hand movement score and the comprehensive hand movement score are obtained, subtract the single hand movement score from a plurality of obtained comprehensive hand movement scores separately to obtain a plurality of listening effort scores, and then obtain the cognitive scoring result through analysis based on a change between the listening effort scores.

9. The hand-eye collaborative auditory cognitive assessment system according to claim 2, wherein the speech task stored in the word and sentence database module comprises a plurality of types of long sentences, short sentences, and words; and the speech task output by the audio output module is some long sentences, short sentences, or words obtained from the word and sentence database module.

10. The hand-eye collaborative auditory cognitive assessment system according to claim 2, wherein the image display module is configured to adjust touch area of the moving region.

* * * * *